United States Patent [19]

Waldmann et al.

[11] Patent Number: 5,789,620
[45] Date of Patent: Aug. 4, 1998

[54] PROCESS FOR THE PREPARATION OF 1,4-BIS(AMINOMETHYL) CYCLOHEXANE

[75] Inventors: Helmut Waldmann, Nideggen; Jürgen Dahmer, Krefeld, both of Germany; Klaus Nachtkamp, Düsseldorf, Russian Federation; Anatoly Bazanov, St. Petersburg, Russian Federation; Alexandre Timofeev, St. Petersburg, Russian Federation; Natalja Zubritskaya, St. Petersburg, Russian Federation; Gennady Terechtchenko, St. Petersburg, Russian Federation

[73] Assignee: Bayer Aktiengesellschaft, Leverkusen, Germany

[21] Appl. No.: 962,072

[22] Filed: Oct. 31, 1997

[30] Foreign Application Priority Data

Nov. 4, 1996 [DE] Germany ............... 196 45 360.7
Nov. 29, 1996 [DE] Germany ............... 196 49 658.6

[51] Int. Cl.$^6$ ............... C07C 209/16
[52] U.S. Cl. ............... 564/447
[58] Field of Search ............... 564/447

[56] References Cited

U.S. PATENT DOCUMENTS

| | | | |
|---|---|---|---|
| 3,143,570 | 8/1964 | Caldwell et al. | 260/563 |
| 3,551,487 | 12/1970 | Bluestein | 260/563 |
| 4,222,961 | 9/1980 | Butte, Jr. et al. | 260/563 D |
| 5,288,911 | 2/1994 | Koppenhoefer | 564/480 |

Primary Examiner—Brian M. Burn
Attorney, Agent, or Firm—Joseph C. Gil; Thomas W. Roy

[57] ABSTRACT

The present invention relates to a process for preparing 1,4-bis(aminomethyl)cyclohexane by reacting a 40 to 80 wt. % aqueous solution of 1,4-bis(hydroxymethyl)cyclohexane with a mixture of hydrogen and ammonia in the presence of a nickel/copper/chromium catalyst at a pressure of 100 to 250 bar and a temperature of 150° to 250° C.

2 Claims, No Drawings

PROCESS FOR THE PREPARATION OF 1,4-BIS(AMINOMETHYL) CYCLOHEXANE

BACKGROUND OF THE INVENTION

1. Field of the Invention

The present invention relates to a process for the preparation of 1,4-bis(aminomethyl)cyclohexane from an aqueous solution of the corresponding dihydroxy compound in the presence of a nickel/copper/chromium catalyst.

2. Description of the Prior Art

It is known to prepare 1,4-bis(aminomethyl)cyclohexane from dicyanobenzene in a two stage process as disclosed, e.g., in DE-A 3,003,730. In the first stage dicyanobenzene is catalytically hydrogenated to produce 1,4-bis(aminomethyl) benzene, which is then catalytically hydrogenated to produce 1,4-bis(aminomethyl)cyclohexane. One disadvantage is that the starting material must be produced with hydrogen cyanide.

U.S. Pat. No. 3,143,570 discloses a cyanide-free process using 1,4-bis-hydroxy-methylcyclohexane as the starting material; however, this process has proven to be an industrially unsatisfactory process.

It is an object of the present invention to provide a simple method for preparing 1,4-bis(aminomethyl)cyclohexane.

This object may be achieved with the process according to the invention described hereinafter.

SUMMARY OF THE INVENTION

The present invention relates to a process for preparing 1,4-bis(aminomethyl)cyclohexane by reacting a 40 to 80 wt. % aqueous solution of 1,4-bis(hydroxymethyl)cyclohexane with a mixture of hydrogen and ammonia in the presence of a nickel/copper/chromium catalyst at a pressure of 100 to 250 bar and a temperature of 150° to 250° C.

DETAILED DESCRIPTION OF THE INVENTION

The finely divided catalyst preferably contains 50 to 60 mole % nickel, 14 to 17 mole % copper and 26 to 33 mole % chromium.

The reaction is performed at a temperature of 150° to 250° C. and a pressure of 100 to 250 bar, preferably 150 to 250 bar, optionally in the presence of an inert gas, such as nitrogen.

EXAMPLES

Example 1

The process was performed in a continuous-flow reactor with a fixed bed catalyst. The reactor was charged with a volume of 100 cm$^3$ of a catalyst containing 57 mole % nickel, 14 mole % copper and 29 mole % chromium and reduced with a stream of nitrogen. The reactants were fed at an hourly rate of 100 liters of hydrogen, 100 cm$^3$ of liquid ammonia and 20 cm$^3$ of a 50% aqueous solution of 1,4-bis(hydroxymethyl)cyclohexane.

The reactor was maintained at a temperature of 190° C. and a pressure of 200 bar while the reaction was carried out. Once the water and ammonia had been removed from the mixture, 9.9 g per hour of a product were obtained containing 60 wt. % of 1,4-bis(aminomethyl)cyclohexane and 20.3 wt. % of 1,4-bis(hydroxymethyl)cyclohexane. Conversion was 80.1% and selectivity for 1,4-bis(aminomethyl) cyclohexane formation was 74.5 mole %.

Example 2

The process and catalyst were the same as in Example 1. The reactants were fed at an hourly flow rate of 100 liters of hydrogen, 100 cm$^3$ of liquid ammonia and 13 cm$^3$ of a 70% aqueous solution of 1,4bis(hydroxymethyl)cyclohexane. The reactor was maintained at a temperature of 190° C. and a pressure of 200 bar. Once the water and ammonia had been removed from the mixture, 8.8 g per hour of a product were obtained containing 71.4 wt. % of 1,4-bis(aminomethyl)-cyclohexane and 11.2 wt. % of 1,4-bis(hydroxymethyl) cyclohexane. Conversion was 89.2% and selectivity for 1,4-bis(aminomethyl)cyclohexane was 78.3 mole %.

Example 3

The process was the same as in Example 1. The reactor was charged with a volume of 100 cm$^3$ of a catalyst powder consisting of 50 mole % nickel, 17 mole % copper and 33 mole % chromium. The reactants were charged at an hourly feed rate of 100 liters of hydrogen, 100 cm$^3$ of liquid ammonia and 13 cm$^3$ of a 50 wt. % aqueous solution of 1,4-bis(hydroxymethyl)cyclohexane. The reactor was maintained at a temperature of 190° C. and a pressure of 200 bar during the reaction. Once the water and ammonia had been removed, 6.4 g per hour of a product were obtained containing 53 wt. % of 1,4-bis(aminomethyl)cyclohexane and 17.8 wt. % of 1,4-bis(hydroxymethyl)-cyclohexane. Conversion was 82.6% converted and selectivity for 1,4-bis (aminomethyl)cyclohexane formation was 63.5 mole %.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing 1,4-bis(aminomethyl) cyclohexane which comprises reacting a 40 to 80 wt. % aqueous solution of 1,4-bis(hydroxymethyl)cyclohexane with a mixture of hydrogen and ammonia in the presence of a nickel/copper/chromium catalyst at a pressure of 100 to 250 bar and a temperature of 150° to 250° C.

2. The process of claim 1 wherein said catalyst contains 50 to 60 mole % nickel, 14 to 17 mole % copper and 26 to 33 mole % chromium.

* * * * *